United States Patent
Wang et al.

(10) Patent No.: US 8,927,566 B2
(45) Date of Patent: Jan. 6, 2015

(54) NOREPINEPHRINE AND SELECTIVE SEROTONIN RECEPTOR BLOCKER AND USE THEREOF

(71) Applicant: Beijing Medisan Technology Co., Ltd., Changping District Beijing (CN)

(72) Inventors: Mingxin Wang, Changping District Beijing (CN); Jinai Liu, Changping District Beijing (CN); Fan Yang, Changping District Beijing (CN); Ailing Wang, Changping District Beijing (CN); Jiguo Sun, Changping District Beijing (CN); Yan Wang, Changping District Beijing (CN); Jin Cui, Changping District Beijing (CN); Lei Ji, Changping District Beijing (CN)

(73) Assignee: Beijing Medisan Technology Co., Ltd., Beijing (CN)

( * ) Notice: Subject to any disclaimer, the term of this patent is extended or adjusted under 35 U.S.C. 154(b) by 0 days.

(21) Appl. No.: 14/360,021

(22) PCT Filed: Nov. 21, 2012

(86) PCT No.: PCT/CN2012/084935
§ 371 (c)(1),
(2) Date: May 22, 2014

(87) PCT Pub. No.: WO2013/075621
PCT Pub. Date: May 30, 2013

(65) Prior Publication Data
US 2014/0343089 A1 Nov. 20, 2014

(30) Foreign Application Priority Data

Nov. 22, 2011 (CN) .......................... 2011 1 0372775
Nov. 19, 2012 (CN) .......................... 2012 1 0470263

(51) Int. Cl.
*A61K 31/4353* (2006.01)
*C07D 491/12* (2006.01)
*C07D 491/147* (2006.01)

(52) U.S. Cl.
CPC ................. *C07D 491/147* (2013.01)
USPC .......................................... 514/287; 546/64

(58) Field of Classification Search
USPC ............................................ 514/287; 546/64
See application file for complete search history.

(56) References Cited

U.S. PATENT DOCUMENTS 4,154,836 A * 5/1979 van der Burg ................ 514/285

FOREIGN PATENT DOCUMENTS

WO 01/26621 A2 10/2000

OTHER PUBLICATIONS

Berge, Stephen M. et al., "Pharmaceutical Salts", Journal of Pharmaceutical Sciences, 66(1): 1-19 (1977).
Zhao, Jingping, "Novel Noradrenergic and Specific Serotoninergic Antidepressant Mirtazapine", Chinese Journal of Psychiatry, 35(4): 253 (2002).
International Search Report, dated Feb. 28, 2013, from corresponding International Patent Application PCT/CN2012/084935, filed Nov. 21, 2012.

* cited by examiner

*Primary Examiner* — Charanjit Aulakh
(74) *Attorney, Agent, or Firm* — Patrick J. Hagan; Dann, Dorfman, Herrell and Skillman

(57) ABSTRACT

The present invention relates to a norepinephrine and selective serotonin receptor blocker and the use thereof. The norepinephrine and selective serotonin receptor blocker is a compound of formula I, or isomers, pharmaceutically acceptable salts or solvates thereof, wherein R1 is selected from the group consisting of C1-6 alkyl, C1-6 alkoxy, C6-10 aralkyl, C6-10 arylalkoxy, C1-6 haloalkyl and C1-6 haloalkoxy; and R2 is one or more groups each independently selected from the group consisting of hydrogen, halogen, C1-6 alkyl, C1-6 alkoxy, nitro, cyano, amino, hydroxyl, C1-6 haloalkyl, and C1-6 haloalkoxy. R3 is one or more groups each independently selected from the group consisting of hydrogen, halogen, C1-6 alkyl, C1-6 alkoxy, nitro, cyano, amino, hydroxyl, C1-6 haloalkyl, and C1-6 haloalkoxy. The compound of the present invention is effective norepinephrine and selective serotonin receptor blocker.

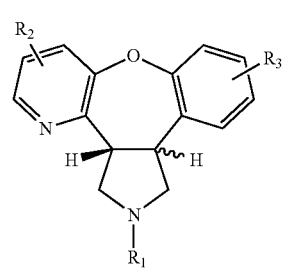

15 Claims, No Drawings

NOREPINEPHRINE AND SELECTIVE SEROTONIN RECEPTOR BLOCKER AND USE THEREOF

This application is a 371 of International Application No. PCT/CN2012/084935, filed Nov. 21, 2012, which claims the benefits of priorities to Chinese patent application No. 201110372775.8 filed on Nov. 22, 2011 and Chinese patent application No. 201210470263.X filed on Nov. 19, 2012. The entire disclosure of each of the aforesaid applications is incorporated by reference in the present application.

TECHNICAL FIELD

The present invention relates to a norepinephrine and selective serotonin receptor blocker and use thereof. Such a medicament for example can be used to treat and/or prevent depressive disorder.

BACKGROUND ART

Depressive disorder is a mood disorder or affective disorder caused by various reasons with depression as the main symptom, and is a group of clinical symptoms or states centering on depressive mood self-experience, which includes down mood in chief, incompatibility with circumstances and may vary from moodiness to inconsolability, or even occur a stupor. Severe ones may develop psychotic symptoms like hallucinations, delusions, etc. For some cases, anxiety and exercise-induced agitation are quite significant. Depressive disorder centers on depressive mood, thinking retardation and decline in volition, with various somatic symptoms present in most cases.

At present the antidepressants used in clinic primarily include the following kinds: the first generation classic antidepressants: including monoamine oxidase inhibitor (MAOI) such as isopropyl hydrazine, Moclobemide, etc., and the tricyclic antidepressants (TCA) such as Imipramine, Amitriptyline, Doxepin and Clomipramine, Maprotiline. The second generation antidepressants: These drugs include selective serotonin reuptake inhibitors and selective serotonin (SSRIs) and norepinephrine dual reuptake inhibitors such as Fluoxetine, Paroxetine, Citalopram, etc. As new drugs have developed rapidly, new drugs come out endlessly, for example venlafaxine, des-venlafaxine and vilazodone, etc. are sequently on sale, but currently selective serotonin reuptake inhibitors are still in chief. Such drugs are the most frequently and widely used in clinical application. The tricyclic antidepressants are the longest used in clinical application and the pharmacologic effects thereof are the most and fullest studied. In short, the main pharmacologic effects of antidepressants are: 1. blocking reuptake of monoamine neurotransmitters (mainly adrenaline (NA) and serotonin (5-HT)), increasing the amount of monoamine in neurosynaptic clefts thereby generating antidepressive effect. 2. Blocking various neurotransmitter receptors, which is unrelated to the therapeutic effect but is the main reason for many adverse reactions. For example blocking acetylcholine M receptor may lead to xerostomia, blurred vision, sinus tachycardia, constipation, urinary retention, glaucoma exacerbation and memory dysfunction, etc.; blocking adrenergic α1 receptors may lead to enhancement of the antihypertensive effect of prazosin, orthostatic hypotension, dizziness, reflex tachycardia; blocking histamine H1 receptors may lead to enhancement of central inhibitory effect, sedation, somnolence, weight gain and decreased blood pressure; blocking dopamine D2 receptors may lead to extrapyramidal symptoms and changes in endocrine, etc.

In "novel noradrenergic and specific serotoninergic antidepressant Mirtazapine, Jingping Zhao, *Chinese Journal of Psychiatry, Vol.* 35, No. 4", disclosed is that as belonging to noradrenergic (NE) and specific 5-hydroxytryptaminergic (5HT) antidepressants (NaSSA), the unique pharmacological effect of mirtazapine is different from all the other antidepressants. Mirtazapine belongs to pyrazine-azepine compounds containing a tetracyclic structure, having levorotation, dextral 2 mirror isomers. The levorotatory form selectively blocks isoreceptors only, while the racemates can not only block isoreceptors but also block self-receptors, thus having most of the pharmacological activities. Demethylated mirtazapine is the only metabolite with pharmacological activity of mirtazapine, just occupying 3%-10% of the drug activity.

Although there are many options on antidepressants currently used in clinic, ideal drugs with desirable therapeutic effect are few. The effective rate of general clinical antidepressants is around 40%~50%, and many antidepressants have serious or relatively serious side effects such as sexual dysfunction, weight gain and cardiovascular side effects. Additionally, for these antidepressants, particularly SSRIs, time (onset) of acting antidepressive effect is usually around 4-8 weeks. These serious side effects greatly affect the confidence of patients with depressive disorder in drug usage.

At present, new methods for treating and/or preventing depressive disorder are still expected in the art.

SUMMARY OF THE INVENTION

The object of the present invention lies in providing a novel norepinephrine and selective serotonin receptor blocker and expecting it to be effectively used in treating and/or preventing depressive disorder. The present invention has surprisingly found that the compounds shown as formula I have effective norepinephrine and selective serotonin receptor blocking effect, based on which the present invention is completed.

In the first aspect of the present invention, provided are the following compounds of formula I,

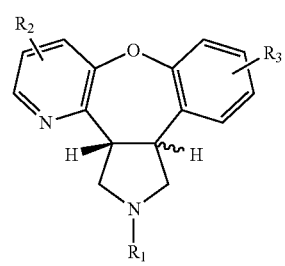

or isomers, pharmaceutically acceptable salts or solvates thereof, wherein

R1 is selected from: C1-6 alkyl, C1-6 alkoxy, C6-10 aralkyl, C6-10 arylalkoxy, C1-6 haloalkyl and C1-6 haloalkoxy;

R2 is one or more groups each independently selected from: hydrogen, halogen, C1-6 alkyl, C1-6 alkoxy, nitro, cyano, amino, hydroxyl, C1-6 haloalkyl, and C1-6 haloalkoxy;

R3 is one or more groups each independently selected from: hydrogen, halogen, C1-6 alkyl, C1-6 alkoxy, nitro, cyano, amino, hydroxyl, C1-6 haloalkyl, and C1-6 haloalkoxy.

Compounds according to one aspect of the present invention, wherein the compounds of formula I preferably are of the following structure:

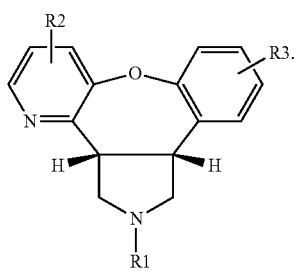

I

Compounds according to one aspect of the present invention, wherein R1 is selected from: C1-6 alkyl and C6-10 aralkyl.

Compounds according to one aspect of the present invention, wherein R2 is one or two groups each independently selected from: hydrogen, halogen, C1-6 alkyl, C1-6 alkoxy, hydroxyl, C1-6 haloalkyl.

Compounds according to one aspect of the present invention, wherein R3 is one or more groups each independently selected from: hydrogen, halogen, C1-6 alkyl, C1-6 alkoxy, hydroxyl.

Compounds according to one aspect of the present invention, wherein R1 is selected from: C1-6 alkyl and C6-10 aralkyl, R2 is a group selected from hydrogen, C1-6 alkyl, hydroxyl, C1-6 haloalkyl, R3 is one or two groups each independently selected from: hydrogen, halogen, C1-6 alkyl and hydroxyl, in which the halogen and halo- is fluorine or chlorine.

Compounds according to one aspect of the present invention, wherein the C1-6 alkyl is a C1-4 alkyl.

Compounds according to one aspect of the present invention, wherein the halogen (halo-) is selected from fluorine, chlorine, bromine, iodine, preferably fluorine and chlorine.

Compounds according to claim 1, which are characterized in that, the isomers include the stereoisomers and structural isomers, etc. of formula I.

A compound according to the first aspect of the present invention, which is a compound selected from:

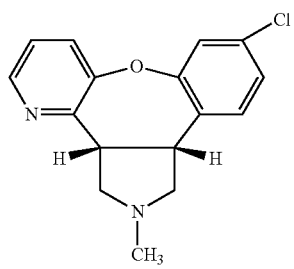

Co.1

-continued

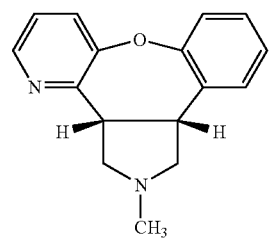

Co.2

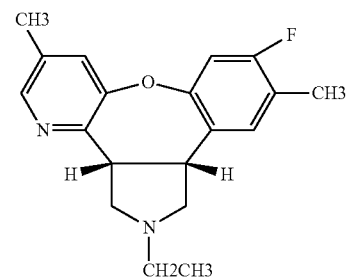

Co.3

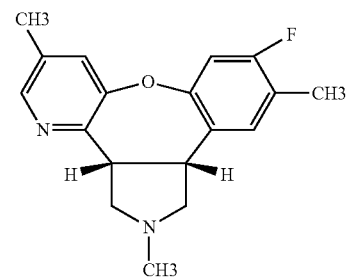

Co.4

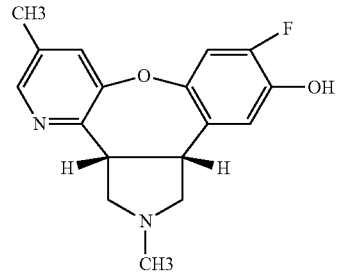

Co.5

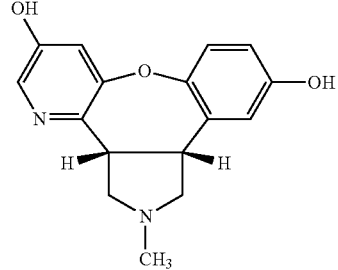

Co.6

-continued

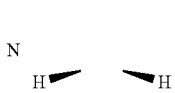
Co.7

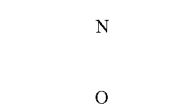
Co.8

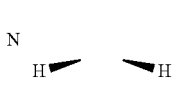
Co.9

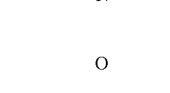
Co.10

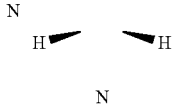
Co.11

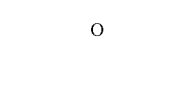
Co.12

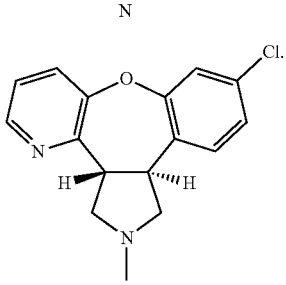

The second aspect of the present invention relates to the method of preparing the compound in the first aspect of the present invention.

The third aspect of the present invention relates to a pharmaceutical composition, comprising the compound of formula I of any one of the first aspect of the present invention, and optionally one or more pharmaceutically acceptable carriers or excipients.

The fourth aspect of the present invention relates to the use of the compound of formula I of any one of the first aspect of the present invention in preparing drugs for treating and/or preventing depressive disorder of a mammal (including human).

The fifth aspect of the present invention relates to a method for treating and/or preventing mammal (including human) depressive disorder in a mammal in need thereof. The method comprises administering a therapeutically effective amount of the compound of formula I of any one of the first aspect of the present invention to a mammal in need thereof.

The sixth aspect of the present invention relates to a pharmaceutical composition for treating and/or preventing depressive disorder of a mammal (including human). The pharmaceutical composition comprises the compound of formula I of any one of the first aspect of the present invention and optionally one or more pharmaceutically acceptable carriers or excipients.

The seventh aspect of the present invention also relates to the compound of formula I of any one of the first aspect of the present invention for treating and/or preventing depressive disorder of a mammal (including human).

Any embodiment in any aspect of the present invention may be in combination with other embodiments, provided that they do not have a contradictory. Further, in any embodiment in any aspect of the present invention, any technical feature may be suitable for the technical feature in other embodiments, provided that they do not have a contradictory.

Hereinafter, the present invention will be further described.

All the documents cited by the present invention are hereby incorporated by reference in their entirety, and if a meaning expressed in these documents is inconsistent with the present invention, the statement of the present invention is taken as the standard. Further, various terms and phrases used in the present invention have the general meaning commonly known by those skilled in the art. Even so, the present invention still expects to illustrate and explain these terms and phrases more detailedly herein. If there are terms and phrases mentioned inconsistent with the meanings commonly known, the meanings stated in the present invention are taken as the standard.

In the method for synthesizing the compound of formula I of the present invention, various raw materials used in the reaction can be prepared by those skilled in the art according to the prior knowledge, or prepared via methods commonly known in the references, or purchased commercially. The intermediates, raw materials, reagents and reaction conditions, etc. used in the reaction scheme above may be properly changed according to the prior knowledge of those skilled in the art. Alternatively, those skilled in the art may also synthesize the other compounds of formula I unlisted specifically in the present invention according to the method in the second aspect of the present invention.

The compound of formula I of the present invention can be used in combination with other active ingredients, provided that it does not produce other adverse effects such as hypersensitive response.

The active compound shown in the formula I of the present invention may be used as an anti-tumor/anti-cancer drug alone, or used in combination with one or more other anti-bacterial drugs. Combination treatment is achieved by simultaneously, sequentially or separately administrating each therapeutic component.

The term "composition" as used herein is intended to include the product comprising a designated amount of each designated ingredient, and any product directly or indirectly produced from combinations of a designated amount of each designated ingredient. In the present invention, the term "composition" may be used interchangeably with "pharmaceutical composition".

The compounds of the present invention may be used in the form of pharmaceutically acceptable salts derived from inorganic acids or organic acids. The phrase "pharmaceutically acceptable salt" refers to a salt within the scope of sound medical judgment suitable for use in contacting with tissues of humans and lower animals without undue toxicity, irritation and hypersensitive response, etc. and is commensurate with a reasonable effect/risk ratio. Pharmaceutically acceptable salts are commonly known in the art. For example, pharmaceutically acceptable salts are described detailedly in S. M. Berge, et al., J. Pharmaceutical Sciences, 1977, 66: 1. The salts may be prepared in situ or separately during the final separation and purification processes of the compound of the present invention, by reacting the free base functionality of the compound of the present invention with a proper organic acid. Representative acid addition salts include but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodic, 2-hydroxylethanesulfonate (isothionate), lactate, maleate, methanesulfonate, nicotinate, 2-naphthalenesulfonate, oxalate, palmitate, pectate, persulfate, 3-phenylpropionate, picrate, pivalate, propionate, succinate, tartrate, thiocyanate, phosphate, glutamate, bicarbonate, p-toluenesulfonate and undecanoate. Likewise, the alkalic nitrogen-containing group may be quaternized with following substances: lower alkyl halides such as chlorides, bromides and iodides of methyl, ethyl, propyl and butyl; dialkyl sulfates such as dimethyl, diethyl, dibutyl and diamyl sulfates; long-chain halides such as chlorides, bromides and iodides of decyl, lauryl, myristyl and stearyl; arylalkyl halides such as benzyl bromide and phenethyl bromide and others. Thus products able to be dissolved or dispersed in water or oil are obtained. Examples of acid used to form pharmaceutically acceptable acid addition salts include inorganic acids such as hydrochloric acid, hydrobromic acid, sulfuric acid and phosphoric acid, and organic acids such as oxalic acid, maleic acid, succinic acid and citric acid.

Alkali addition salts may be prepared in situ during the final separation and purification processes of the compound of the present invention, by reacting the carboxyl-containing moiety in the compound of the present invention with a proper alkali. The alkali is exemplified as a hydroxide, carbonate or bicarbonate of a pharmaceutically acceptable metal cation, or ammonia or an organic primary amine, secondary amine or tertiary amine Pharmaceutically acceptable salts include but are not limited to the salts based on alkali metal or alkaline-earth metal cations such as lithium, sodium, potassium, calcium, magnesium and aluminum, etc., and non-toxic quaternary ammonium and amine cations including ammonium, tetramethyl ammonium, tetraethyl ammonium, methyl ammonium, dimethyl ammonium, trimethyl ammonium, triethyl ammonium, diethyl ammonium and ethyl ammonium, etc. Other representative organic amines for forming the alkali addition salts include ethylenediamine, ethanol amine, diethanol amine, piperidine and piperazine, etc.

The compounds of formula I of the present invention also include the isomers, racemates, enantiomers, diastereomer, enantiomer enrichments, solvates and esters thereof. The compounds of formula I of the present invention and the isomers, racemates, enantiomers, diastereomer, enantiomer enrichments, solvates and esters thereof also may also be transformed into solvates, for example hydrates and alcoholates, etc. The aforementioned compounds also may be prodrugs or the forms able to release said active ingredients after metabolic change in vivo. Selecting and preparing a suitable prodrug derivation is a commonly known technology for those skilled in the art. In general, for the purpose of the present invention, solvated forms with pharmaceutically acceptable solvents such as water, ethanol and the like are equivalent to unsolvated forms.

The actual dosage level of each active ingredient in the composition of the present invention may be changed so that the resulting amount of active compounds can effectively direct to a specific patient, composition and mode of administration obtain a desired therapeutic response. The dosage level must be designated according to the activity of the specific compound, administration route, the severity of conditions under treatment as well as conditions and anamnesis of patients to be treated. However, the practice in the art is that a dosage of compounds begins with a lower level than that required for desired therapeutic effect and then gradually increases until obtaining the desired effect.

When used for the aforementioned treatment and/or prevention or other treatments and/or preventions, the therapeutically and/or prophylactically effect amount of a compound of the present invention may be used in pure form or used in the form of pharmaceutically acceptable ester or prodrug (in the case that these forms exist). Alternatively, the compound may be administrated as a pharmaceutical composition containing the object compound with one or more pharmaceutically acceptable excipients. The term "a therapeutically and/or prophylactically effect amount" of the compound of the present invention refers to an enough amount of compound suitable for use in treatment disorder with any medical therapeutically and/or prophylactically reasonable effect/risk ratio. But it should be understood that the total daily dose of the compound and composition of the present invention must be determined by attending physician within the scope of sound medical judgment. For any specific patient, the specific therapeutically effect dosage level must be determined according to various factors, which include the disorder to be treated and the severity of the disorder; the activity of the specific compound employed; the specific compound employed; age, weight, general health condition, gender and diet of the patient; the administration time, administration route and excretion rate of the specific compound employed; treatment duration; drugs used in combination with or simultaneously with the specific compounds employed; and the similar factors commonly known in the medical art. For example, the practice of the present art is that a dosage level of compounds begins with a lower level than that required for desired therapeutic effect and then increases until obtaining the desired effect. In general, the dosage of the compound of formula I of the present invention for a mammal particularly human may be between 0.001~1000 mg/kg body weight/day, such as between 0.01~100 mg/kg body weight/day, or such as between 0.01~10 mg/kg body weight/day.

By applying pharmaceutical carriers well known by those skilled in the art, the pharmaceutical composition containing an effective amount of the compound of the present invention may be prepared. Therefore, the invention also provides a pharmaceutical composition containing the compound of the present invention formulated together with one or more non-toxic pharmaceutically acceptable carriers. The pharmaceutical composition may be particularly formulated as a solid or liquid form for oral administration, for parenteral injection, or for rectal administration.

The pharmaceutical composition may be formulated as many dosage forms for convenient administration, for example oral formulations (such as tablets, capsules, solutions or suspensions); injectable formulations (such as injectable solutions or suspensions, or injectable dry powder, able to be used immediately by adding water for injection prior to injection). The carriers used in the pharmaceutical composition include: binders used in oral preparations (such as starch, typically corn, wheat or rice starch, gelatin, methyl cellulose, sodium carboxymethyl cellulose and/or polyvinylpyrrolidone), diluents (such as lactose, dextrose, sucrose, mannitol, sorbitol, cellulose and/or glycerol), lubricants (such as silica, talc, stearic acid or a salt thereof, typically magnesium stearate or calcium stearate, and/or polyethylene glycol), and if needed, also contained are disintegrants such as starch, agar, alginic acid or a salt thereof, typically sodium alginate, and/or an effervescent mixtures, solubilizers, stabilizers, suspending agents, no coloring agents and corrigents, etc., preservatives, solubilizers and stabilizers, etc. used in injectable formulations; matrix, diluent, lubricants and preservatives, etc. used in topical formulations. Pharmaceutical formulations may be administered via oral or parenteral (e.g., intravenous, subcutaneous, intraperitoneal or topical) route. If some drugs are unstable under the conditions of stomach, it may be formulated as enteric-coated tablets.

More particularly, the pharmaceutical composition of the present invention may be administrated to a human or other mammal by oral, rectal, parenteral, enteral, intravaginal, intraperitoneal, topical (such as by powders, ointments or drops), buccal administrations, or administrated as a oral spray or nasal spray. As used herein, the term "parenteral" refers to the administration modes including intravenous, intramuscular, intraperitoneal, intrasternal, subcutaneous and intraarticular injection and infusion.

The composition suitable for parenteral injection may comprise physiologically acceptable sterile aqueous or non-aqueous solutions, dispersants, suspensions or emulsions, and sterile powders for use in reconstituting into sterile injectable solutions or dispersants. The examples for suitable aqueous or non-aqueous carriers, diluents, solvents or vehicles include water, ethanol, polyols (propylene glycol, polyethylene glycol and glycerol, etc.), vegetable oils (such as olive oil), injectable organic esters such as ethyl oleate and suitable mixtures thereof.

These compositions may also contain adjuvant agents such as preservatives, wetting agents, emulsifiers and dispersants. By means of various anti-bacterial and antifungal agents, for example, parabens, trichlorotert-butanol, phenol and sorbic acid, etc., the effect of preventing microorganisms can be ensured. It is also intended to include an isotonic agent, for example sugars, sodium chloride, etc. By using a substance able to delay absorption, for example aluminum monostearate and gelatin, extended absorption of the injectable pharmaceutical form can be achieved.

A suspending agent for example ethoxylated isostearyl alcohol, polyoxyethylene sorbitol and polyoxyethylene sorbitan esters, microcrystalline cellulose, partial aluminum hydroxide, bentonite, agar and gum tragacanth, or a mixture of these substances, etc. may also be contained in the suspensions except for the active compounds.

In some cases, to extend the effect of drugs, slowing the absorption of subcutaneous or intramuscular injectable drugs is expected. This can be achieved by using liquid suspensions of a poorly water-soluble crystalline or amorphous substance. As such, drug absorption rate depends on dissolution rate, while the dissolution rate may also depend on crystal size and crystalline form. Alternatively, delayed absorption of the drug form in parenteral administration is achieved by dissolving or suspending the drug in an oil vehicle.

Injectable depot formulation forms may be prepared by forming microcapsule matrix of drug in biodegradable polymers such as polylactide-polyglycolide. According to the ratio of the drug to the polymers and properties of the specific polymers employed, drug release rate is to be controlled. Other examples for biodegradable polymers include poly(orthoesters) and poly(anhydrides). Injectable depot formulations also can be prepared by embedding the drug into liposomes or microemulsions compatible with body tissues.

Injectable formulations may be sterilized for example by filtration with a bacteria filter or by incorporating a sterilizing agent in the form of sterile solid composition. The solid composition may be dissolved or dispersed in sterile water or other sterile injectable medium just prior to administration.

The compound of the present invention or the composition thereof may employ oral method or parenteral administration mode. Oral administration may be tablets, capsules, coating agents, and parenteral administration formulations include injections and suppositories, etc. These formulations are prepared in accordance with methods well known by those skilled in the art. In order to manufacture tablets, capsules, coating agents excipients being used are excipients in conventional use, for example starch, gelatin, gum acacia, silica, polyethylene glycol, solvents used in liquid dosage forms such as water, ethanol, propylene glycol, vegetable oils (such as maize oil, peanut oil and olive oil, etc.). In the formulations containing the compounds of the present invention, there are also other adjuvants, such as surfactants, lubricants, disintegrants, preservatives, corrigents and pigments, etc. The dosage of the compound of formula I of the present invention contained in tablets, capsules, coating agents, injections and suppositories is calculated based on amount of the compound present in a unit dosage form. In the unit dosage form the general amount of the compound of formula I of the present invention is 0.01-5000 mg, a preferred unit dosage form contains 0.1-500 mg, and a more preferred unit dosage form contains 1-300 mg. Specifically, the solid dosage forms for oral administration provided by the present invention include capsules, tablets, pills, powders and granules. In such solid dosage forms, the active compound may be mixed with at least one inert and pharmaceutically acceptable excipient or carrier such as sodium citrate or dicalcium phosphate and/or the following substances: a) fillers or extenders such as starch, lactose, sucrose, glucose, mannitol and silicic acid; b) binders such as carboxymethylcellulose, alginates, gelatin, polyvinylpyrrolidone, sucrose and gum acacia; c) moisturizers such as glycerol; d) disintegrants such as agar, calcium carbonate, potato or tapioca starch, alginic acid, some silicates, and sodium carbonate; e) solution blockers such as paraffin; f) absorption accelerators such as quaternary ammonium compounds; g) wetting agents such as cetyl alcohol and glycerol monostearate; h) adsorbents such as kaolin and bentonite and i) lubricants such as talc, calcium stearate, magnesium stearate, solid polyethylene glycols, sodium lauryl sulfate, and mixtures thereof. In cases of capsules, tablets and pills, the dosage form may also comprise buffering agents.

A solid composition of similar type uses excipients for example lactose and polyethylene glycol with high molecular weight, which may be used as an infilling in soft capsules and hard capsules.

The solid dosage forms of tablets, dragees, capsules, pills and granules may be prepared together with coatings and casing materials such as enteric coating materials and other coating materials commonly known in the field of medical formulations.

These solid dosage forms may optionally contain opacifying agents, and the constitutions thereof can also make them release active ingredients merely or preferably in a certain site of intestinal tract optically in delayed mode. The examples of embedding composition that can be used include substances with high molecular weight and waxes. If appropriate, the active compounds can be formulated as microcapsules form with one or more excipients above.

Liquid dosage forms for oral administration include pharmaceutically acceptable emulsions, solutions, suspensions, syrups and elixirs. Liquid dosage forms, in addition to the active compounds, also contain inert diluents commonly used in the art e.g. water or other solvents, solubilizers and emulsifiers for example ethanol, isopropanol, ethyl carbonate, ethyl acetate, benzyl alcohol, benzyl benzoate, propylene glycol, 1,3-butanediol, dimethylformamide, oils (particularly cottonseed oil, peanut oil, maize oil, germ oil, olive oil, castor oil and sesame oil), glycerol, tetrahydrofurfuryl alcohol, polyethylene glycols and sorbitan fatty acid esters and mixtures thereof. In addition to inert diluents oral compositions may also contain excipients, such as wetting agents, emulsifiers and suspending agents, sweetening agents, corrigents and flavoring agents.

Compositions for rectal or vaginal administration are preferably suppositories. Suppositories may be prepared by mixing the compounds of the present invention with suitable non-irritating excipients or carriers such as cocoa butter, polyethylene glycols or suppository waxes. They are solid at room temperature but liquid at body temperature therefore able to melt in rectal cavity or vaginal cavity then releasing the active compounds.

The compounds of the present invention and the compositions thereof are also considered for topical administration. The dosage forms for topically administrating the compounds of the present invention include powders, sprays, ointments and inhalants. Under a sterile condition the active compounds are mixed with pharmaceutically acceptable carriers and any required preservatives, buffers or propellants. Ophthalmic formulations, ophthalmic ointments, powders and solutions are also considered within the scope of the present invention.

The compounds of the present invention may also be administered in the form of liposomes. As commonly known in the art, liposomes are usually prepared with phospholipids or other lipid substances. Liposomes are formed of single-layer or multi-layer hydration liquid crystals dispersed in an aqueous medium. Any non-toxic physiologically acceptable and metabolizable lipid able to form liposomes may be used. The compositions of the present invention in liposomes form, in addition to the compounds of the present invention may also contain stabilizers, preservatives, excipients, etc. The preferred lipids are natural and synthetic phospholipids and phosphatidylcholine (lecithin), which may be used separately or together. Methods of forming liposomes are commonly known in the art. See for example Prescott, Ed., Methods in Cell Biology, Volume XIV, Academic Press, New York, N.Y. (1976), p. 33.

The norepinephrine and selective serotonin receptor blockers expected to be provided by the present invention can maintain the good antidepressive therapeutic effect of current drugs such as Mirtazapine or the antidepressive therapeutic effect is superior to current drugs such as Mirtazapine; alternatively the norepinephrine and selective serotonin receptor blockers expected to be provided by the present invention maintain the good side effect properties of Mirtazapine without significant sexual dysfunction and emesis side effect; they are expected to have no significant somnipathy side effect, and have a certain therapeutic effect on somnipathy; these compounds are expected to have a better therapeutic effect on anxiety symptom of patients, and improve the weight gain side effect fundamentally or control the side effect thereof to a minimal level; these compounds are expected to have good safety, such as, no cardiovascular side effects at a therapeutic dose, high safety at a overdose, no blood cachexia, small interactions with drugs and no inducement of acute onsets.

The method for determining the activities of some exemplary compounds of the present invention as a norepinephrine and selective serotonin receptor blocker is shown in the tests below. These results indicate that the compounds of the present invention are effective norepinephrine and selective serotonin receptor blockers and can be used to treat or prevent depressive disorder.

EMBODIMENTS

Hereinafter the present invention is further illustrated through the specific preparation embodiments and biological tests. However, it should be understood that these examples and test examples are merely for the use of more detailed and specific illustration, and should not be construed to be used in any form of limiting the present invention.

The present invention conducts a general and/or specific description on the materials used in the tests and test methods. Although many materials and operation methods used to achieve the purposes of the present invention are commonly known in the art, the present invention still makes a description detailedly as possible here. It should be clear to those skilled in the art, hereinafter if without particular description, the materials and operation methods used in the present invention are commonly known in the art.

EXAMPLE 1

Preparation of the Compound of the Following Formula (Co.1)

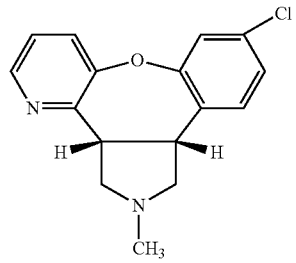

The synthetic route is as follows:

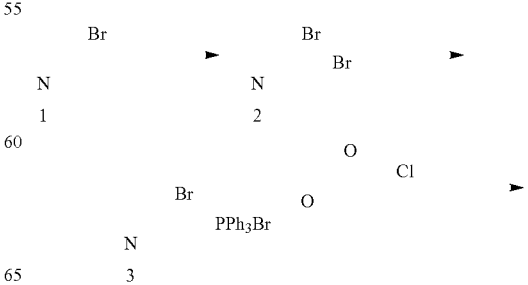

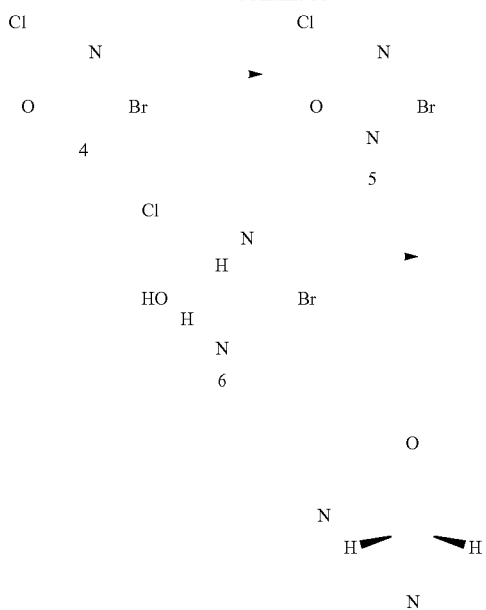

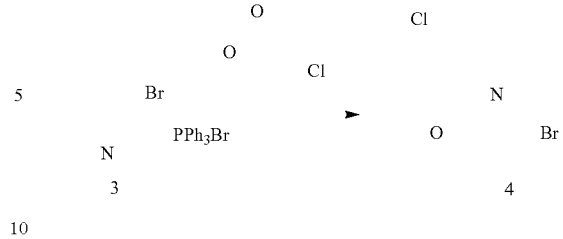

The compound 3 above (25 g), 9.2 g of 4-chloro-2-methoxy benzaldehyde, 13.5 g of potassium carbonate were added to a reaction flask with nitrogen protection, followed by sequent addition of water (10 ml), DMF (90 ml), heated to 95° C. and tracked by TLC. After the reaction was completed, the mixture was cooled to room temperature, added with 100 ml of water, 200 ml of ethyl acetate and extracted for three times. The combined organic phase was washed with water, saturated brine, dried, filtered, and distilled under reduced pressure. The resulting substance was recrystallized with ethanol to obtain a pale yellow solid compound 4 (7.0 g, yield 45%). $^1$H-NMR (CDCl3): 3.52 (s 3H) 6.82 (d H) 6.89 (d H) 6.75 (s H) 6.78 (d H) 7.10 (d H) 7.61 (t H) 8.04 (d H) 8.81 (d H).

Specific steps:

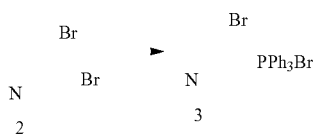

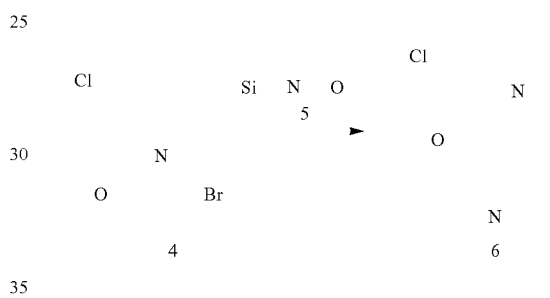

Operations: 100 g of compound 1 (3-bromo-2-methyl pyridine, TCI (Shanghai) Chemical Industry Co., Ltd.) was dissolved in carbon tetrachloride. 155 g of N-bromosuccinimide and 5 g of benzoyl peroxide were added and refluxed for 48 h under nitrogen protection and cooled to filter off insoluble substances. After being added with an appropriate amount of ethyl acetate, the organic phase was washed with diluted hydrochloric acid once, then washed with a saturated aqueous solution of sodium bicarbonate, and finally washed and extracted with saturated brine. The organic phase was dried, filtered and distilled under reduced pressure to obtain a pale yellow oily substance, isolated by column chromatography to obtain compound 2 (43 g, yield 30%). MS: m/z 251.8.

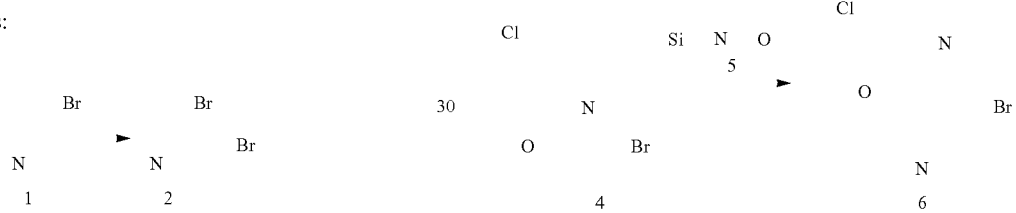

Compound 2 above was dissolved in toluene. 54 g of triphenyl phosphine was added, under nitrogen protection, heated and refluxed to react overnight. After the reaction was completed, the mixture was cooled to room temperature and filtered. The resulting solid substance was fully washed with ethyl acetate, filtered and dried to obtain the yellow solid compound 3 (25 g, yield 28%). MS: m/z 514, 512.

Synthesis of Compound 5: (Chloromethyl)trimethylsilane (100 ml) and 40% aqueous methylamine solution were added to a reaction flask, heated to reflux for about 6 hours, and cooled to room temperature after the reaction was completed. After the reaction system was layered the water phase was cooled to 5 degree and solid potassium hydroxide (34 g) was added thereto. The aqueous phase was extracted with 1:1 n-heptane and tent-butyl ether (200 ml) and the organic phase was combined. The product from reduced pressure distillation was distilled at about 95-100 degree. Finally methyl trimethylsilyl methylamine was obtained (38 g, 50% yield).

In an aqueous formaldehyde solution (37%, 8.5 g) cooled by ice water the product above (20.5 g) was slowly added dropwise. The reaction temperature was controlled below 5 degree. 14 ml of formaldehyde and 12 g of potassium carbonate were added to the reaction system. Approximately after one hour reacting, after the reaction system was layered, in the organic phase, 2 g of potassium carbonate was added and stirred for two hours. Potassium carbonate was filtered off. The organic phase was distilled under reduced pressure (20 mbar) to collect the product at 45 degree (10 g, yield 36%). 1H-NMR (CDCl3): 0.00 (s 9H) 2.0 (s 2H) 2.30 (s 3H) 3.25 (s 3H) 3.88 (s 2H).

Synthesis of Compound 6: at about 30 degree compound 4 (7 g) was dissolved in 50 ml of toluene. After a few drops of trifluoroacetic acid were added, compound 5 was added dropwise over about an hour. After the reaction was completed, the mixture was concentrated in vacuum to become an oily substance, which was dissolved in 30 ml of methanol and added with 10 ml of a 20% aqueous potassium hydroxide solution. After stirring for 30 minutes, the pH value was adjusted to 8-9 with 3N hydrochloric acid. After stirred for 30 minutes, the mixture was filtered. The solid product was dried in vacuum to obtain compound 6 (5.5 g, yield 67%). 1H-NMR (CDCl3): 2.27 (s 3H) 2.62 (d 4H) 3.35 (m 2H) 3.60 (s 3H) 6.96 (d H) 6.72 (s H) 6.75 (d H) 7.57 (m H) 8.10 (d H) 8.80 (d H).

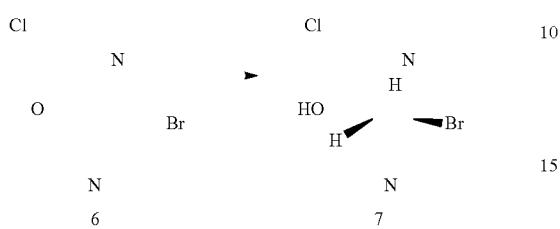

In a reaction flask 5.5 g of compound 6 was added to 100 ml of hydrobromic acid (48%), and refluxed for about six hours. After the reaction was completed, the mixture was cooled to room temperature. A solid was precipitated and filtered and the solid was adjusted to a pH value of 6-7 with 10% sodium hydroxide. Dichloromethane was added for extraction. The organic phases were combined, washed with water, saturated brine, dried, filtered and concentrated under reduced pressure to obtain compound 7 (4.5 g, yield 85%). 1H-NMR (CDCl3): 2.28 (s 3H) 2.60 (d 4H) 3.28 (m 2H) 6.63 (s H) 6.72 (d H) 6.98 (d H) 7.53 (t H) 8.05 (d H) 8.80 (d H).

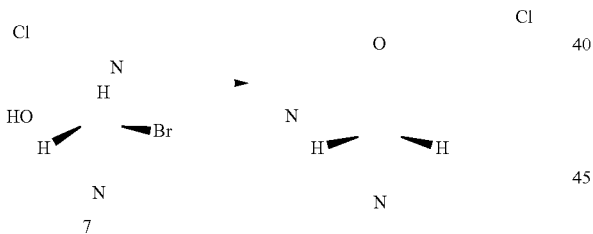

In a reaction flask compound 7 (4.5 g), cesium carbonate (9.9 g), cuprous iodide (0.25 g), N,N-dimethyl-glycine (0.5 g) and 50 ml of DMF were added. Under nitrogen protection, the temperature was around 120 degree and the reaction was tracked by TLC. After the reaction was completed, the mixture was cooled to room temperature and added with 100 ml of water and 200 ml of ethyl acetate. The aqueous phase was extracted with ethyl acetate respectively for three times. The organic phases were combined, dried, filtered and distilled under reduced pressure. The resulting solid substance was recrystallized repeatedly to obtain the final compound (2.8 g, yield 80%). 1HNMR (CDCl3): 2.30 (s 3H) 2.49 (d 4H) 3.35 (m 2H) 6.56 (s H) 6.75 (d H) 6.85 (d H) 7.30 (d H) 7.41 (t H) 8.38 (d H). Ms: m/z=287, 289 (an isotope of chlorine).

EXAMPLE 2

Preparation of the Compound of the Following Formula (Co.2)

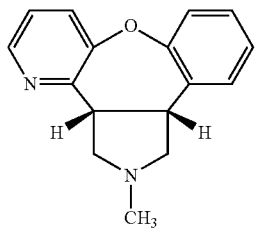

The same synthetic route and method as Example 1 were used. The difference lied in replacing 4-chloro-2-methoxy benzaldehyde with 2-methoxy benzaldehyde to react with compound 3, thereby obtaining the final compound.

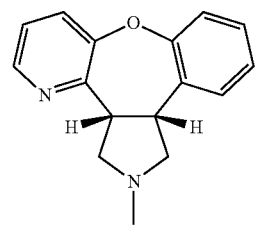 [SMILES: CN1C[C@@H]2c3ncccc3Oc3ccccc3[C@@H]2C1]

1HNMR (CDCl3): 2.26 (s 3H) 2.5 (m 4H) 3.32 (t 2H) 7.08 (t H) 7.10 (d H) 7.13 (t H) 7.20 (t H) 7.35 (d H) 7.23 (d H) 8.15 (d H).

EXAMPLE 3

Preparation of the Compound of the Following Formula (Co.3)

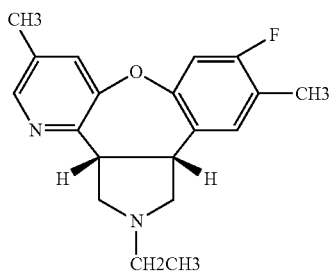

The same synthetic route and method as Example 1 were used. The differences lied in replacing 3-bromo-2-methyl pyridine with 3-bromo-2,5-dimethyl pyridine, replacing 4-chloro-2-methoxy benzaldehyde with 4-fluoro-2-methoxy-5-methyl benzaldehyde to react with compound 3 and replacing methylamine with ethylamine in the synthesis of compound 5, thereby obtaining the final compound.

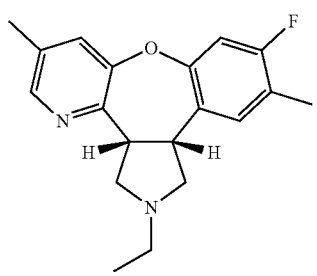

1HNMR (CDCl3): 1.02 (t 3H) 2.30 (s 3H) 2.35 (s 3H) 2.40 (m 2H) 2.5 (m 4H) 3.28 (t 2H) 6.85 (s H) 6.92 (s H) 7.32 (s H) 8.20 (s H).

EXAMPLE 4

Preparation of the Compound of the Following Formula (Co.4)

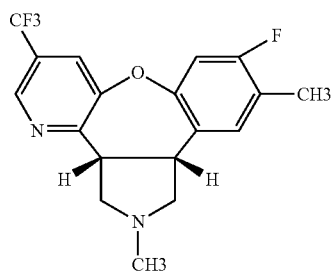

The same synthetic route and method as Example 1 were used. The differences lied in replacing 3-bromo-2-methyl pyridine with 3-bromo-2-methyl-5-trifluoromethyl pyridine and replacing 4-chloro-2-methoxy benzaldehyde with 4-fluoro-2-methoxy-5-methyl benzaldehyde to react with compound 3, thereby obtaining the final compound.

1HNMR (CDCl3): 2.20 (s 3H) 2.32 (s 3H) 2.5 (m 4H) 3.32 (t 2H) 6.85 (s H) 6.90 (s H) 7.18 (s H) 8.20 (s H).

EXAMPLE 5

Preparation of the Compound of the Following Formula (Co.5)

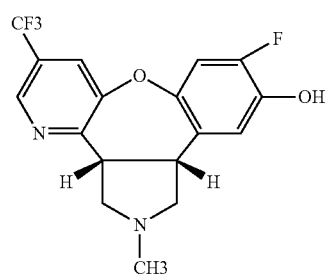

The same synthetic route and method as Example 1 were used. The differences lied in replacing 3-bromo-2-methyl pyridine with 3-bromo-2-methyl-5-trifluoromethyl pyridine, replacing triphenyl phosphine with triethyl phosphite to react with the brominated compound 2 to synthesize the form of 3-bromo-5-trifluoromethyl pyridyl methyl diethyl phosphate (compound 3) in the second step of the reactions, replacing 4-chloro-2-methoxy benzaldehyde with 4-fluoro-2-methoxy-5-methyl benzaldehyde to react with the compound 3, and finally using hydrobromic acid to demethylate thereby obtaining the final compound.

1HNMR (CDCl3): 2.23 (s H) 2.5 (m 4H) 3.25 (t 2H) 6.78 (s H) 6.82 (s H) 7.19 (s H) 8.24 (s H).

EXAMPLE 6

Preparation of the Compound of the Following Formula (Co.6)

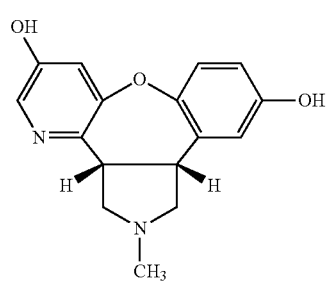

The same synthetic route and method as Example 1 were used. The differences lied in replacing 3-bromo-2-methyl pyridine with 3-bromo-2-methyl-5-methoxy pyridine, replacing triphenyl phosphine with triethyl phosphite to react with the brominated compound 2 to synthesize the form of 3-bromo-5-methoxy pyridyl methyl diethyl phosphate (compound 3) in the second step of the reactions, replacing 4-chloro-2-methoxy benzaldehyde with 2-hydroxyl-5-methoxy benzaldehyde to react with the compound 3, and finally using hydrobromic acid to demethylate thereby obtaining the final compound.

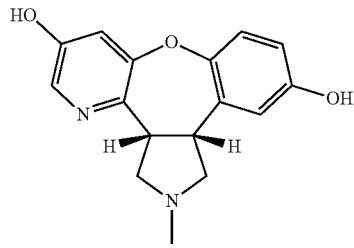 [SMILES: CN1C[C@@H]2c3ncc(O)cc3Oc3ccc(O)cc3[C@@H]2C1]

1HNMR (CDCl3): 2.23 (s 3H) 2.5 (m 4H) 3.25 (t 2H) 6.70 (d H) 6.73 (d H) 6.82 (s H) 6.93 (s H) 8.12 (s H).

EXAMPLE 7-10

The same synthetic route and method as Example 1 were used. The differences lied in that in the synthesizing of compound 5, using ethylamine, n-propylamine, n-butylamine and benzylamine as raw materials to replace methylamine, the following several compounds with different substituents were sequently synthesized:

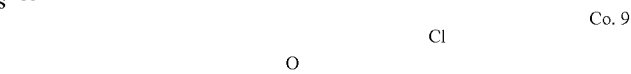

Wherein R=methyl, ethyl, propyl, butyl and benzyl.

According to the synthetic route above, the related final compounds were respectively obtained.

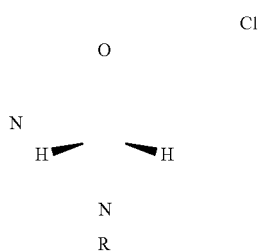

Wherein R=methyl, ethyl, propyl, butyl and benzyl.

Wherein except for Co.1 synthesized in Example 1, the other compounds were:

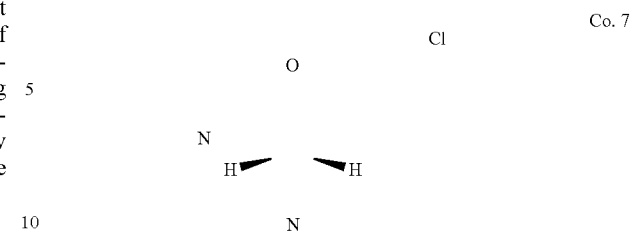

1HNMR (CDCl3): 1.2 (t 3H) 2.50 (m 2H) 2.56 (d 4H) 3.35 (m H) 3.28 (m H) 6.56 (s H) 6.70 (d H) 6.89 (d H) 7.36 (t H) 8.35 (d H). m/z=301, 303 (an isotope of chlorine)

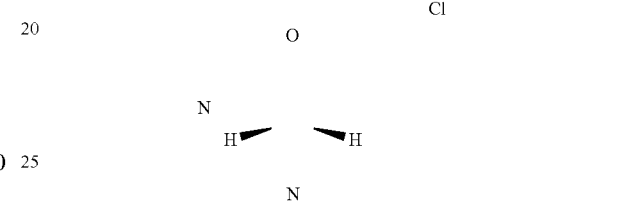

1HNMR (CDCl3): 0.96 (t 3H) 1.42 (m 2H) 2.60 (t 2H) 2.58 (d 4H) 3.25 (m H) 3.29 (m H) 6.56 (s H) 6.68 (d H) 6.90 (d H) 7.28 (d H) 7.35 (t H) 8.34 (d H). m/z=315, 317 (an isotope of chlorine)

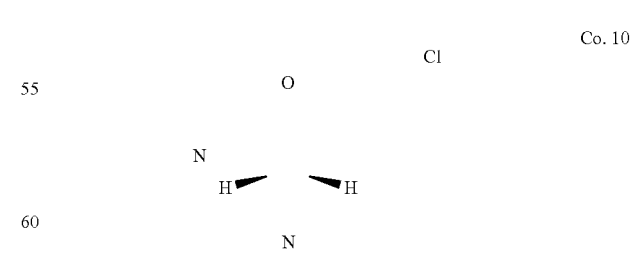

1HNMR (CDCl3): 0.93 (t 3H) 1.30 (m 2H) 1.35 (m 2H) 2.34 (t 2H) 2.58 (d 4H) 3.24 (m H) 3.28 (m H) 6.64 (s H) 6.72 (d H) 6.92 (d H) 7.25 (d H) 7.35 (t H) 8.35 (d H). m/z=329, 331 (an isotope of chlorine)

1HNMR (CDCl3): 2.58 (d 4H) 3.25 (m H) 3.28 (m H) 6.56 (s H) 6.72 (d H) 6.88 (d H) 7.03 (d 2H) 7.07 (t H) 7.10 (t 2H) 7.25 (d H) 7.35 (t H) 8.34 (d H). m/z=363, 365 (an isotope of chlorine)

EXAMPLE 11

Preparation of Compounds of the Following Formulas (Co.1 and Co.12)

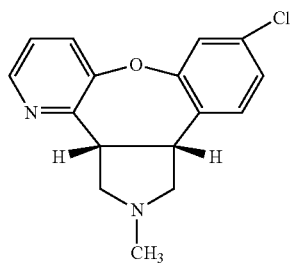

The synthetic route is as follows:

Specific steps:

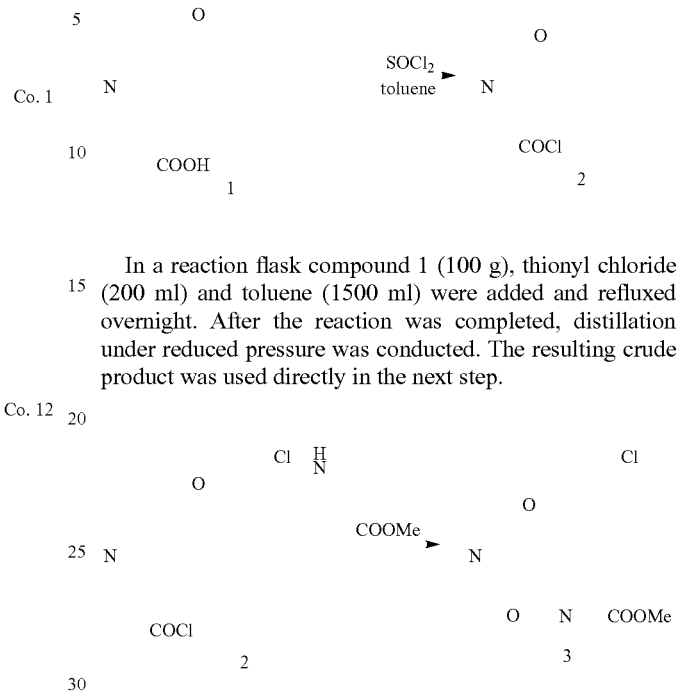

In a reaction flask compound 1 (100 g), thionyl chloride (200 ml) and toluene (1500 ml) were added and refluxed overnight. After the reaction was completed, distillation under reduced pressure was conducted. The resulting crude product was used directly in the next step.

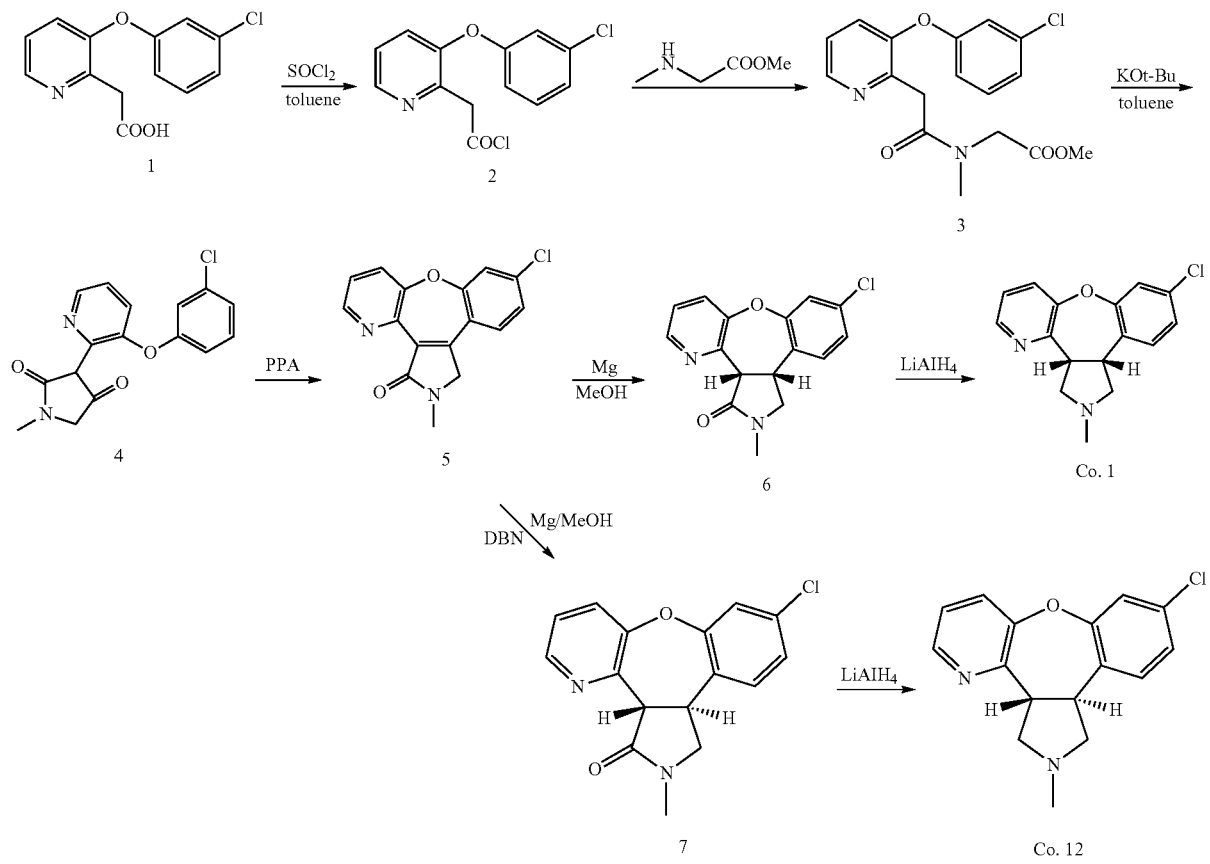

The resulting crude compound 2 as well as methylamino ethyl acetate (43 g), triethylamine (46 g) and DMF (1000 ml) were added to a reaction flask, reacted at room temperature overnight. After completed, the reaction was quenched with the addition of water and the mixture was extracted with ethyl acetate for three times. The organic phases were combined, dried, filtered and concentrated to obtain compound 3 (90 g, yield 69%). IH-NMR (CDCl3): 2.35 (s 3H) 3.43 (s 3H) 3.57 (s 2H) 4.08 (s 2H) 6.57 (d H) 6.62 (s H) 6.73 (d H) 7.08 (t H) 7.31 (d H) 7.34 (t H) 8.39 (d H).

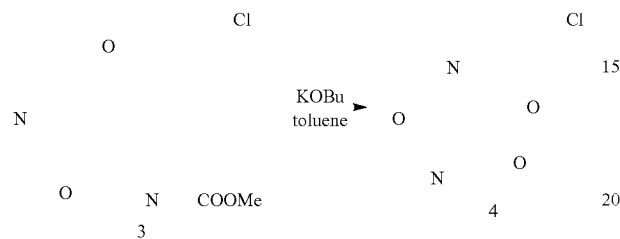

90 g of compound 3 and 58 g of potassium tert-butoxide were added to a reaction flask, and then added with 1000 ml of toluene as the solvent. The reaction was refluxed overnight and monitored by TLC. After the reaction was completed, the mixture was cooled to room temperature and quenched with the addition of water. Then the aqueous phases were extracted with ethyl acetate for three times. The organic phases and aqueous phases were combined, washed with brine, dried, filtered and distilled under reduced pressure. The resulting solid substance was recrystallized in a mixed solvent of ethyl acetate and petroleum ether to obtain compound 4 (62 g, yield 76%). 1H-NMR (CDCl3): 2.85 (s 3H) 4.32 (s 2H) 4.56 (s H) 6.58 (d H) 6.65 (s H) 6.82 (d H) 7.08 (t H) 7.32 (d H) 7.29 (t H) 8.35 (d H).

62 g of compound 4 was added to a 1 liter reaction flask, added with 300 ml of polyphosphoric acid and heated to 150 degree, reacting for about 20 hours. After the reaction was completed, the solution was cooled to about 50 degree and poured into ice water with a great quantity of solid precipitated, which was filtered. The solid was recrystallized with acetone and water to obtain compound 5 (30 g, yield 51%). 1H-NMR (CDCl3): 2.85 (s 3H) 3.98 (s 2H) 6.58 (s H) 6.75 (d H) 7.12 (d H) 7.28 (d H) 7.29 (t H) 8.35 (d H).

30 g of compound 5 as well as magnesium powder (7.2 g), iodine (5 g) were reacted in a mixed solution of methanol and toluene with a reaction temperature below 40 degree. After the reaction was completed, the mixture was filtered and distilled under reduced pressure. The resulting crude product was isolated by column chromatography to obtain compound 6 (19.8 g, yield 67%). 1H-NMR (CDCl3): 2.85 (s 3H) 3.59 (d 2H) 3.62 (m H) 3.88 (d H) 6.60 (s H) 6.69 (d H) 6.88 (d H) 7.30 (d H) 7.35 (t H) 8.35 (d H).

8 g of compound 6, lithium aluminum hydride (2.8 g) and aluminium trichloride (5.6 g) were added to a reaction flask, the solvent was a mixture solvent of tetrahydrofuran and toluene. The reaction temperature was controlled below 15 degree. After completed, the reaction was quenched by slowly adding water dropwise and the mixture was filtered. The aqueous phase was extracted with ethyl acetate for three times. The organic phases were combined, dried, filtered and distilled under reduced pressure. The resulting crude product was recrystallized in ethyl acetate to obtain the target product Co.1 (4.8 g, yield 63%). 1H-NMR (CDCl3): 2.25 (s 3H) 2.56 (d 4H) 3.25 (m H) 3.28 (m H) 6.60 (s H) 6.67 (d H) 6.83 (d H) 7.30 (d H) 7.33 (t H) 8.32 (d H). MS: m/z=287, 289 (an isotope of chlorine).

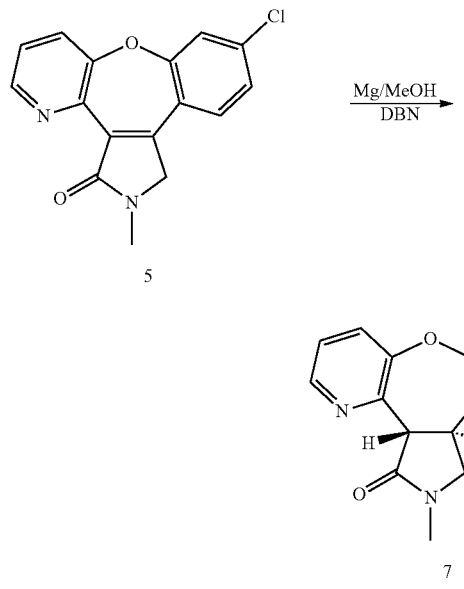

30 g of compound 5 as well as magnesium powder (7.2 g), iodine (5 g) were reacted in a mixed solution of methanol and toluene with a reaction temperature below 40 degree. After the reaction was completed as well as the post-processing was accomplished, the mixture was concentrated under reduced pressure. The concentrate was dissolved in 500 ml of toluene, added with 5-diazabicyclo[4.3.0] non-5-ene (DBN, 50 ml) and stirred for 1 h, added with water and acetic acid to adjust the pH value to about 4. The organic layer was separated, washed with water, concentrated under reduced pressure and subjected to column chromatography (toluene:ethyl acetate=95:5). The part containing cis-form was proceeded with DBN isomerization operation repeatedly, purified with methanol to obtain product 7 (11.6 g, yield 39%). 1H-NMR (CDCl3): 2.95 (s 3H) 3.58 (d 2H) 3.65 (m H) 3.88 (d H) 6.67 (s H) 6.69 (d H) 6.89 (d H) 7.32 (d H) 7.38 (t H) 8.34 (d H).

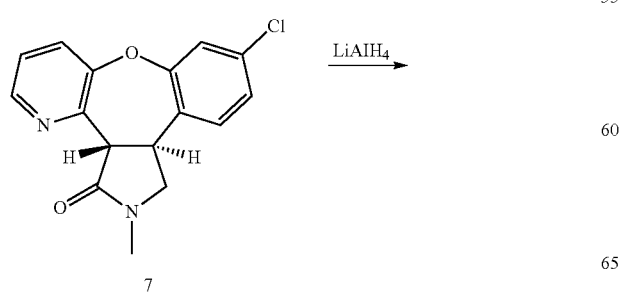

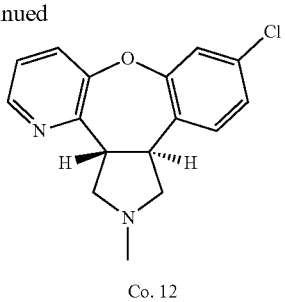

8 g of compound 7, lithium aluminum hydride (2.8 g), aluminium trichloride (5.6 g) were added to a reaction flask, the solvent was a mixture solvent of tetrahydrofuran and toluene. The reaction temperature was controlled below 15 degree. After completed, the reaction was quenched by slowly adding water dropwise and the mixture was filtered. The aqueous phase was extracted with ethyl acetate for three times. The organic phases were combined, dried, filtered and distilled under reduced pressure. The resulting crude product was recrystallized in ethyl acetate to obtain the target product Co.12 (5.4 g, yield 71%). 1H-NMR (CDCl3): 2.28 (s 3H) 2.56 (d 4H) 3.29 (m H) 3.33 (m H) 6.57 (s H) 6.71 (d H) 6.80 (d H) 7.31 (d H) 7.33 (t H) 8.36 (d H). MS: m/z=287, 289 (an isotope of chlorine).

EXAMPLE 12

Preparation of the Compound of the Following Formula (Co.11)

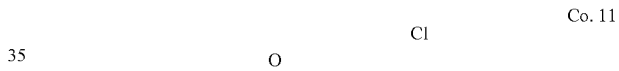

The same synthetic route and method as Example 11 were used. The differences lied in using compound

as the raw material to replace compound 1 used therein, finally obtaining the target product

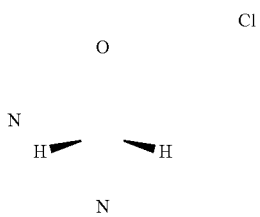

1H-NMR (CDCl3): 2.38 (s 3H) 2.59 (d 4H) 3.22 (m H) 3.29 (m H) 6.30 (d H) 6.78 (d H) 6.81 (s H) 7.30 (d H) 7.42 (t H) 8.35 (d H). MS: m/z=287, 289 (an isotope of chlorine).

Preliminary evaluation on the pharmaceutical effect of the synthesized compounds by biological tests:

Test example 1: effect of the compounds on immobility time of tail suspension in mice Animals used for experiments were adult male ICR mice weighing 18~25 g, housed in 8 pcs/cages, regulated with a 12/12 hour light/dark cycle, maintained at a constant temperature of 23±1° C. and a humidity of 50~60% and allowed ad libitum access to rodent chow and water. After animals were purchased from the experimental animal center and performed an adaptive housing, the experiment was allowed to start.

After animal adaptive housing, all the animals were randomly divided into three groups:

Group one: negative control group, intraperitoneally injected with 1% DMSO in physiological saline (10.0 ml/kg, i.p.);

Group two: experimental drug group, the mice were intraperitoneally injected respectively with different doses of the test compound Co.1: 0.1, 0.5, 1, 5 and 10 mg/kg, i.p., the drug was formulated in 1% DMSO in physiological saline;

Group three: positive drug control group, the mice were intraperitoneally injected with Desipramine (20 mg/kg, i.p., the drug was formulated in 1% DMSO in physiological saline).

The experiment employed Shanghai Jiliang animal behavior video analysis system, wherein the experimental environment was kept absolutely silent, when grabbing animals and administrating, movements were gentle to minimize adverse reactions of mental condition and emotion brought by external stimulus. 60 minutes after dosing, the site 20 mm from the tail end was fixed and the mice were hung upside-down in an activity box for 6 minutes. The immobility time in later 4 minutes was analyzed.

Results: the experimental results indicated that, compound Co.1 (1.0, 5.0 and 10 mg/kg, i.p.) significantly inhibited the immobility time of tail suspension in mice (P<0.05-0.01, Dunnett't test, compared to the negative control group), while compound Co.1 (0.1 and 0.5 mg/kg, i.p.) had no effect on the immobility time of tail suspension in mice. The inhibitory effect on the immobility time of tail suspension in mice of the tested compound was similar to the positive drug Desipramine (P<0.05-0.01, Dunnett't test, compared to the Desipramine control group).

Conclusions: the experimental results indicated that the compound had relatively good antidepressive effect and the antidepressive intensity thereof was similar to a positive drug.

Test example 2: effect of the compounds on immobility time of forced swimming in mice Animals used for experiments were adult male ICR mice weighing 18~25 g, housed in 8 pcs/cages, regulated with a 12/12 hour light/dark cycle, maintained at a constant temperature of 23±1° C. and a humidity of 50~60% and allowed ad libitum access to rodent chow and water. After animals were purchased from the experimental animal center and performed an adaptive housing, the experiment was allowed to start.

After animal adaptive housing, all the animals were randomly divided into three groups:

Group one: negative control group, intraperitoneally injected with 1% DMSO in physiological saline (10.0 ml/kg, i.p.);

Group two: experimental drug group, the mice were intraperitoneally injected respectively with different doses of test compound Co.3: 0.1, 0.5, 1, 5 and 10 mg/kg, i.p., the drug was formulated in 1% DMSO in physiological saline;

Group three: positive drug control group, the mice were intraperitoneally injected with Desipramine (20 mg/kg, i.p., the drug was formulated in 1% DMSO in physiological saline).

The mice were placed in a large beaker with a height of about 40 cm and an internal diameter of about 19 cm, loaded with water with a temperature of 24~25° C. inside. The water level reached 22 cm height (Porsolt et al., 1977). The mice were placed in the beaker loaded with water for 15 minutes to be adapted to the environment in water. The mice were removed, dried, and placed in a dry animal cage, which was irradiated by low light above. 15 minutes later the animals were injected with drugs or control substances, put back into the original animal cages, and replaced back to the original animal room. On the next day, the animals were transferred to laboratory and placed for one hour to be adapted to the environment. The animals were injected with drugs or control substances. 30 minutes, or 60 minutes later, the mice were placed into a beaker loaded with water, and immobility time of animals within 5 minutes was measured. The standard for immobility of animals was that, animals floated on the water without any activity, or animals just made some simple movements to keep their heads above water. Between the two experiments, the water in the beaker must be replaced with clean water.

Results: the experimental results indicated that, compound Co.3 (0.5, 1.0, 5.0 and 10 mg/kg, i.p.) significantly extended the immobility time of forced swimming in mice (P<0.05-0.01, Dunnett't test, compared to the negative control group). This effect was stronger than the positive drug Desipramine (P<0.05, Dunnett't test, compared to the Desipramine control group). Conclusions: the experimental results indicated that the tested compound had relatively good antidepressive effect and the antidepressive effect thereof was better than a positive drug.

Test example 3: effect of the compounds on spontaneous activity in mice

Animals used for experiments were adult male ICR mice weighing 18~25 g, housed in 8 pcs/cages, regulated with a 12/12 hour light/dark cycle, maintained at a constant temperature of 23±1° C. and a humidity of 50~60% and allowed ad libitum access to rodent chow and water. After animals were purchased from the experimental animal center and performed an adaptive housing, the experiment was allowed to start.

After animal adaptive housing, all the animals were randomly divided into three groups:

Group one: negative control group, intraperitoneally injected with 1% DMSO in physiological saline (10.0 ml/kg, i.p.);

Group two: experimental drug group, the mice were intraperitoneally injected respectively with different doses of test compound Co.1: 0.1, 0.5, 1, 5 and 10 mg/kg, i.p., the drug was formulated in 1% DMSO in physiological saline.

Group three: positive drug control group, the mice were intraperitoneally injected with Desipramine (20 mg/kg, i.p., the drug was formulated in 1% DMSO in physiological saline).

The experiment employed Shanghai Jiliang animal behavior video analysis system, wherein the experimental environment was kept absolutely silent, when grabbing animals and administrating, movements were gentle to minimize adverse reactions of mental condition and emotion brought by external stimulus. 60 minutes after dosing, the mice were placed in a spontaneous activity box, which was placed in an absolutely silent environment. The spontaneous activity box was connected to a recording apparatus and the activity conditions of mice within 30-60 minutes were recorded. The effects of drug or control substances on spontaneous activity in mice were determined.

Results: each test dose of the compound had no significant effect on spontaneous activity in mice (P>0.05, Dunnett't test, compared with the negative control group).

Conclusions: the experimental results indicated that the compound had no undue sedation.

The invention claimed is:

1. A Compound of formula I, or isomers, pharmaceutically acceptable salts or solvates thereof, wherein R1 is selected from the group consisting of C1-6 alkyl, C1-6 alkoxy, C6-10 aralkyl, C6-10 arylalkoxy, C1-6 haloalkyl and C1-6 haloalkoxy;

R2 is one or more groups each independently selected from the group consisting of hydrogen, halogen, C1-6 alkyl, C1-6 alkoxy, nitro, cyano, amino, hydroxyl, C1-6 haloalkyl, and C1-6 haloalkoxy;

R3 is one or more groups each independently selected from the group consisting of hydrogen, halogen, C1-6 alkyl, C1-6 alkoxy, nitro, cyano, amino, hydroxyl, C1-6 haloalkyl, and C1-6 haloalkoxy.

2. The compound according to claim 1, wherein R1 is selected from the group consisting of C1-6 alkyl and C6-10 aralkyl.

3. The compound according to claim 1, wherein R2 is one or two groups each independently selected from the group consisting of hydrogen, halogen, C1-6 alkyl, C1-6 alkoxy, hydroxyl, and C1-6 haloalkyl.

4. The compound according to claim 1, wherein R3 is one or more groups each independently selected from the group consisting of hydrogen, halogen, C1-6 alkyl, C1-6 alkoxy, and hydroxyl.

5. The compound according to claim 1, wherein the halogen is selected from the group consisting of fluorine, chlorine, bromine, iodine, and the halo- is selected from the group consisting of fluorine, chlorine, bromine, iodine, preferably fluorine and chlorine.

6. The compound according to claim 5, wherein the halogen is selected from the group consisting of fluorine and chlorine.

7. The compound according to claim 5, wherein the halo- is selected from the group consisting of fluorine and chlorine.

8. The compound according to claim 1, wherein R1 is selected from the group consisting of C1-6 alkyl and C6-10 aralkyl, R2 is a group selected from the group consisting of hydrogen, C1-6 alkyl, hydroxyl, C1-6 haloalkyl, R3 is one or two groups each independently selected from the group consisting of hydrogen, halogen, C1-6 alkyl and hydroxyl, in which the halogen and halo- is fluorine or chlorine.

9. The compound according to claim 1, which is a compound selected from the group consisting of Co.6 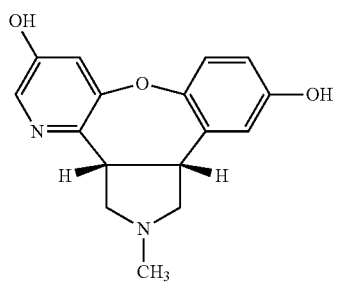

Co.7 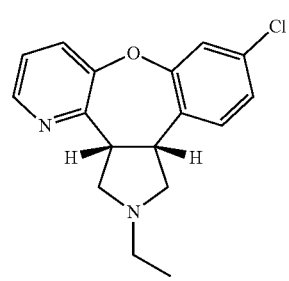

Co. 8 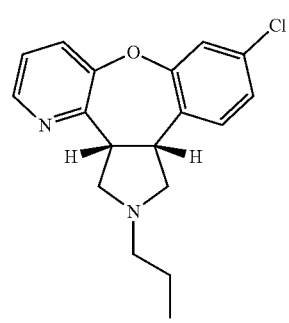

Co. 9 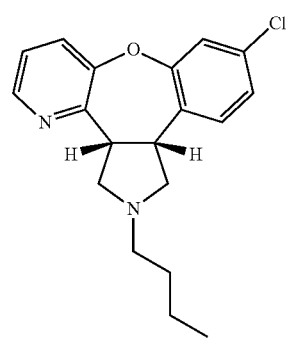

Co. 10 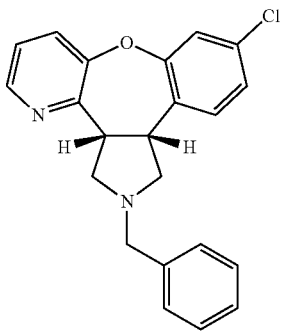

Co. 11 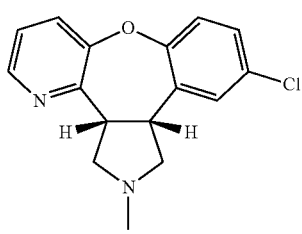

Co.12 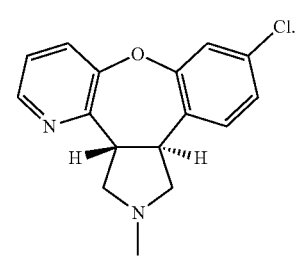

10. A pharmaceutical composition, which comprises the compound of formula I according to claim 1.

11. The pharmaceutical composition according to claim 10, which further comprises one or more pharmaceutically acceptable carriers or excipients.

12. A pharmaceutical composition for treating depressive disorder of a mammal, which comprises the compound of formula I according to claim 1.

13. The pharmaceutical composition for treating depressive disorder of a mammal according to claim 12, which further comprises one or more pharmaceutically acceptable carriers or excipients.

14. A method for treating depressive disorder in a mammal in need thereof, which comprises administering a therapeutically effective amount of the compound of formula I according to claim 1 to a mammal in need thereof.

15. The method according to claim 14, wherein said mammal is a human.

* * * * *